United States Patent
Berekaa

(10) Patent No.: US 10,358,665 B2
(45) Date of Patent: Jul. 23, 2019

(54) METHOD FOR PRODUCING POLYHYDROXYALKANOATE BY FED-BATCH CULTURE OF BACILLUS BACTERIA IN A MEDIUM CONTAINING DATE SYRUP

(71) Applicant: Imam Abdulrahman bin Faisal University, Dammam (SA)

(72) Inventor: Mahmoud M. Berekaa, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 15/259,674

(22) Filed: Sep. 8, 2016

(65) Prior Publication Data

US 2018/0066291 A1   Mar. 8, 2018

(51) Int. Cl.
*C12P 7/62* (2006.01)

(52) U.S. Cl.
CPC .................. *C12P 7/625* (2013.01)

(58) Field of Classification Search
None
See application file for complete search history.

(56) References Cited

U.S. PATENT DOCUMENTS

2004/0191878 A1   9/2004   Bordoloi et al.

FOREIGN PATENT DOCUMENTS

| CN | 101760485 A | 6/2010 |
|----|-------------|--------|
| ID | 2013/00064 A | 7/2011 |
| WO | WO 2012/075051 A1 | 7/2012 |

OTHER PUBLICATIONS

Akaraonye et al. Biotechnol J. Feb. 2012;7(2):293-303 (abstract).*
Prabhu et al. Antonie Van Leeuwenhoek. Jan. 2010;97(1):41-50.*
Omar et al. Biotechnology Letters (2001), 23(14), 1119-1123.*
Kanjanachumpol et al. Bioprocess Biosyst Eng. Oct. 2013;36(10):1463-74.*
Berekaa et al. African Journal of Microbiology Research vol. 6(9), pp. 2101-2108, Mar. 9, 2012. (Year: 2012).*
M.A.Khiyami et al., "Polyhydroxyalkanoates production via Bacillus PCS biofilm and date palm syrup" https://www.researchgate.net/publication/234100637_Polyhydroxyalkanoates_production_via_Bacillus_PCS_biofilm_and_date_palm_syrup, vol. 5 ,Issue 14, Jul. 8, 2011, pp. 3312-3320.
S.A.Ataei et al., "Isolation of PHA—Producing Bacteria from Date Syrup Waste" http://onlinelibrary.wiley.com/doi/10.1002/masy.200850903/abstract, vol. 261, Issue. 1. , Aug. 2008, pp. 11-16.
S.Omar et al., "Optimization of cell growth and poly(3-hydroxybutyrate) accumulation on date syrup by a Bacillus megaterium strain" http://link.springer.com/article/10.1023%2FA%3A1010559800535, vol. 12, Issue.14, Jul. 2001, pp. 1119-1123.

* cited by examiner

*Primary Examiner* — Christian L Fronda
(74) *Attorney, Agent, or Firm* — Oblon, McClelland, Maier & Neustadt, L.L.P.

(57) ABSTRACT

A method for producing a polyhydroxyalkanoate in a bacteria of a *Bacillus* species, the method comprising culturing the bacteria of the *Bacillus* species in a growth medium in the presence of a date syrup, said bacteria biosynthetically producing the polyhydroxyalkanoate intracellularly; and isolating the polyhydroxyalkanoate from the bacteria.

20 Claims, 1 Drawing Sheet

Specification includes a Sequence Listing.

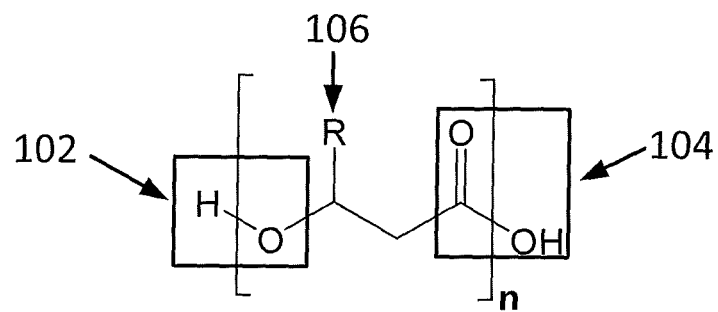

METHOD FOR PRODUCING POLYHYDROXYALKANOATE BY FED-BATCH CULTURE OF BACILLUS BACTERIA IN A MEDIUM CONTAINING DATE SYRUP

BACKGROUND OF THE INVENTION

Technical Field

The present invention relates to a method of producing polyhydroxyalkanoates from a *Bacillus* species of bacteria with a date syrup feedstock in a fed-batch cultivation technique.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Every day thousands of tons of petroleum-based plastic waste accumulate in the environment, resulting in growing non-biodegradable landfills and escalating waste disposal costs. A solution to this problem is to use biodegradable alternatives to plastics, one such alternative being polyhydroxyalkanoates (PHA), a family of high-performance, highly marketable biodegradable polymers possessing excellent physical properties suitable for a wide range of industrial applications.

PHA is a macromolecule produced by bacterial fermentation. It is a polyester molecule composed of hydroxyl fatty acid monomer subunits. It is UV-stable, resistant to extreme temperatures, and resistant to permeation by water. Unlike petroleum-based plastics that can take centuries to degrade, PHA-based plastics are completely biodegradable when placed in decomposition environments such as landfills or composting sites. Furthermore, if accidentally placed in the earth's oceans, PHA-based plastics degrade quickly without any harmful effects on sea life or the greater ocean environment from chemical residues or other pollutants. In addition to these properties, PHA is also biocompatible, gradually breaking down harmlessly without inducing an inflammatory response in the body.

PHA production is based on renewable resources as opposed to diminishing fossil fuel stockpiles. PHA can be commercially produced in bacterial fermentation processes using substrates to drive microorganism growth and PHA synthesis. These substrates can be agricultural products, e.g., sugar and fatty acids.

The most common form of PHA produced is a blend of polyhydroxybutyrate (PHB) and polyhydroxyvalerate (PHV), which has properties very similar to polypropylene currently found in many containers, housewares, and automotive parts. Because of its biocompatibility, PHA-based plastics can also be used in biological applications, such as medical sutures, tissue repair devices, or for other biomedical uses.

The favorable properties of PHA provide incentives to develop efficient ways of producing PHA using biological systems. Despite the advantages of using PHA plastics, the high price of PHA compared to the low price of petrochemical-based plastics has significantly limited its widespread use. Several factors are critical for economic production of PHA: substrate costs, fermentation time, and efficiency of downstream processing. The current production processes, dependent on genetically modified organisms (GMOs), have numerous limitations, such as requiring strict environmental controls, sterile operating conditions, and relatively expensive feedstocks.

Thus, there exists a need to develop cost-effective and efficient biological systems to produce PHA, in particular, microorganisms capable of producing high yields of PHA from inexpensive, readily available, and renewable feedstock.

In view of the forgoing, one objective of the present invention is to provide a method for producing polyhydroxyalkanoate in a bacterial species with date syrup as a feedstock by a fed-batch process.

BRIEF SUMMARY OF THE INVENTION

According to a first aspect, the present disclosure relates to a method for producing a polyhydroxyalkanoate in bacteria of a *Bacillus* species, the method includes culturing the bacteria of the *Bacillus* species in a growth medium comprising date syrup, said bacteria biosynthetically producing the polyhydroxyalkanoate intracellularly and isolating the polyhydroxyalkanoate from the bacteria.

In some implementations of the method, the polyhydroxyalkanoate is polyhydroxybutyrate and/or polyhydroxyvalerate.

In some implementations of the method, the polyhydroxyalkanoate produced in the bacteria accumulates in an intracellular inclusion body of the bacteria.

In some implementations of the method, the date syrup includes 15%-20% fructose, 20%-40% glucose, and 0.1%-50% sucrose, each relative to the total volume of the date syrup.

In some implementations of the method, the date syrup is 0.5%-7% v/v relative to a total volume of the growth medium and the bacteria.

In some implementations of the method, the growth medium further includes 0.1%-5% v/v molasses or palm sugar, relative to the total volume of the growth medium and the bacteria.

In some implementations of the method, the growth medium includes 0.1 g/L-10 g/L of nutrient broth, 0.1 g/L-1 g/L of magnesium sulfate heptahydrate, and 1 mL/L-5 mL/L trace element solution, and the growth medium has a pH of 6.9-7.4.

In some implementations of the method, the trace element solution includes 0.05 g/L-1 g/L of zinc sulfate heptahydrate, 0.01-1.0 g/L of manganese chloride tetrahydrate, 0.01 g/L-1.0 g/L copper sulfate tetrahydrate.

In some implementations of the method, the culturing includes growing the bacteria at a growth temperature of 25° C.-38° C. under agitation in a fed-batch process vessel.

In some implementations of the method, the bacteria is cultured for 20 hours-84 hours in a fed-batch phase in which the date syrup is administered to the bacteria at a limiting level in the amount of 0.1%-5% v/v relative to a volume of the bacteria in the fed-batch process vessel to force the bacteria to synthesize polyhydroxyalkanoate.

In some implementations of the method, the limiting level is administered in a pulse feeding, a shot feeding, a linearly modulated feeding, an exponentially modulated feeding, or a constant feeding during the fed-batch phase.

In some implementations, the method further includes reducing the growth temperature to an ambient temperature of 20° C.-24° C. after the fed-batch phase.

In some implementations of the method, the isolating includes separating the bacteria from the growth media, resuspending the bacteria in a detergent media, freezing the bacteria in the detergent media, reheating the bacteria in the detergent media to 30° C.-40° C. to form lysed bacteria and a supernatant comprising the polyhydroxyalkanoate, sonicating the lysed bacteria in the detergent media, and separating the supernatant from the lysed bacteria.

In some implementations of the method, the secondary detergent is at least one selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethylammonio)-1-propanesulfonate, and n-Octyl-β-D-thioglucopyranoside.

In some implementations of the method, the detergent media includes at least one detergent selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethylammonio)-1-propanesulfonate, and n-Octyl-β-D-thioglucopyranoside, a chaotropic agent, and a buffer, wherein the buffer has a pH of 5-8.

In some implementations of the method, the chaotropic agent is at least one selected from the group consisting of butanol, ethanol, guanidinium chloride, lithium perchlorate, lithium acetate, magnesium chloride, phenol, propanol, thiourea, and urea.

In some implementations of the method, the detergent media further includes a lysozyme.

In some implementations, the method further involves sonicating after adding the secondary detergent.

In some implementation of the method, the separating is achieved by centrifugation.

In some implementations of the method, a temperature of the freezing is −50° C. to −80° C.

The foregoing paragraphs have been provided by way of general introduction, and are not intended to limit the scope of the following claims. The described embodiments, together with further advantages, will be best understood by reference to the following detailed description.

BRIEF DESCRIPTION OF DRAWINGS

FIG. 1 a general structure of polyhydroxyalkanoate polymer with a generalized number of units in the polymer where n is 1000-55000.

DETAILED DESCRIPTION OF THE EMBODIMENTS

Throughout the specification ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

An aspect of the present disclosure relates to a method for producing a polyhydroxyalkanoate in bacteria of a *Bacillus* species. In one embodiment, the *Bacillus* species is collected from Dammam City, Saudi Arabia. *Bacillus* is a genus of gram-positive, rod-shaped (*bacillus*) bacteria and a member of the phylum Firmicutes. *Bacillus* species can be obligate aerobes, which are oxygen reliant, or facultative anaerobes, which the ability to be aerobic or anaerobic. *Bacillus* species may be obtained from soil, deep oceans, ocean vents, aquatic areas, waste water treatment reservoirs, or sewage reservoirs. *Bacillus* species employed in the presently disclosed method may include, but are not limited to *Bacillus subtilis, Bacillus pumilus, Bacillus alvei, Bacillus brevis, Bacillus megaterium, Bacillus circulans, Bacillus amyloliquefaciens,* and *Bacillus thuringiensis*. In some embodiments *Bacillus* species has a percentage of sequence similarity or sequence identity relative to *Bacillus* species identified by accession number HQ124332, is 50%-99%, 55%-95%, 60%-90%, 65%-85%, or 70%-80%. BLASTN may be used to identify a polynucleotide sequence having the percentage of sequence similarity or sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered/masked. Default settings are described by and incorporated by reference to http://blast.ncbi.nlm.nih.gov/Blast.cgi?PROGRAM=blastn&BLAST_PROGRAMS=megaBlast&PAGE_TYPE=BlastSearch&SHOW_DEFAULTS=on&LINK_LOC=blasthome (last accessed Jul. 29, 2016).

In some embodiments the bacteria of the present disclosure may be combined with non-*Bacillus* bacteria including, but not limited to *Aeromonas hydrophila, Thiococcus pfennigii,* of *Pseudomonas putida* to generate polyhydroxyalkanoate.

The method includes culturing the bacteria of the *Bacillus* species in a growth medium in the presence of date syrup, said bacteria biosynthetically producing the polyhydroxyalkanoate intracellularly and isolating the polyhydroxyalkanoate from the bacteria. In some implementations of the method, the polyhydroxyalkanoate (PHA) may include, but is not limited to polyhydroxybutyrate (PHB), polyhydroxyvalerate (PHV), poly-4-hydroxybutyrate (P4HB), polyhydroxyvalerate (PHV), polyhydroxyhexanoate (PHH), and polyhydroxyoctanoate (PHO).

PHA may be produced in microorganisms by biosynthetic processes carried out by specialized enzyme complexes called synthases. Synthases carry out enzyme catalyzed β-oxidation steps to convert long chain alkanes into fatty acids. A PHA synthase may use a sequential series of enzymes to convert a monosaccharide to monomer units polymerized to form a PHA. PHA are categorized by the number of sequential carbon atoms in the repeating units or monomer units that compose the polymer. In the art, PHA having monomer units of three to five sequential carbon atoms is referred to as a short chain length PHA. Further, in the art PHA having monomer units of six to 14 sequential carbon atoms is referred to as a medium chain length PHA. In some implementations synthases and substrates may be configured to produce monomer units of PHA at lengths greater than 14 carbons, but less than 25 carbons. An example of a small chain length PHA is poly(3-hydroxybutyrate), poly(3-hydroxybutyrate-co-3-hydroxyvalerate), poly(3-hydroxybutyrate-co-3-hydroxyvalerate-co-3-hydroxyvalerate). Examples of medium chain length PHA is poly(6-hydroxyhexanoate), poly(3-hydroxyoctanoate), or poly(3-hydroxyheptanoate-co-6-hydroxyhexanoate). The number of monomeric units may be about 1000-55000, about 1200-50000, about 1500-45000, about 2500-40000, about 5000-35000, about 7500-30000, about 10000-25000, about 12500-22500, or about 15000-20000.

A general structure of PHA is depicted in FIG. 1, which generalizes the number of units in the polymer which may be polymerized by either the hydroxyl group 102 end or the carboxylic group 103 end. Further, FIG. 1 depicts an R group 106 may be a number of alkyl groups such as linear alkyls (methyl, ethyl, propyl, butyl, pentyl, hexyl, heptyl, octyl, nonyl, decyl, undecyl, dodecyl, tridecyl, etc.), branched alkyls (isopropyl, isobutyl, t-butyl, etc.), cycloalkyls, phenyl groups, combinations thereof or a hydrogen. Further, the R group 106 may include, but is not limited to a saturated alkyl or unsaturated alkyl, an hydroxyl, a carboxylic acid, an amine, an amide, a guanidinium, a sulfate, a nitrate, and/or a phosphate.

In some implementations of the method, the PHA produced may be branched. Relative to total reactive functional groups in the PHA, a degree of branching may be about 0.1%-90%, about 1%-85%, about 5%-80%, about 10%-75%, about 15%-70%, about 20%-65%, about 20%-60%, about 25%-55%, about 30%-50%, or about 35%-45%. In some implementations of the method, the PHA produced may have a weight-average molecular weight of about 80000 g/mol-700000 g/mol, about 90000 g/mol-650000 g/mol, about 100000 g/mol-600000 g/mol, about 150000 g/mol-550000 g/mol, about 200000 g/mol-500000 g/mol, about 250000 g/mol-450000 g/mol, or about 300000 g/mol-400000 g/mol. In some implementations of the method, the PHA produced may have a number-average molecular weight of about 50000 g/mol-250000 g/mol, about 75000 g/mol-200000 g/mol, about 100000 g/mol-175000 g/mol, or about 125000 g/mol-150000 g/mol.

In the present method, date syrup is a source of food in the growth medium for the bacteria to produce PHA. In some implementations of the method, a volume of the date syrup is in a ratio relative to a volume of the growth medium and the bacteria of about 0.5%-7%, about 1%-5%, or about 2%-3%. In some implementations of the method, the date syrup may include sugars, proteins, and ash. A sugar volume relative to a total volume of date syrup may be about 0.5%-95%, about 1%-90%, about 5%-85%, about 10%-80%, about 15%-75%, about 20%-70%, about 30%-60%, or about 40%-50%. A protein volume relative to the total volume of date syrup may be about 1%-10%, about 1.5%-9.5%, about 2%-8%, about 2.5%-7%, about 3%-6%, or about 4%-5%. An ash volume relative to the total volume of date syrup may be about 0.1%-5%, about 0.5%-4.5%, about 1%-4%, about 1.5%-3.5%, or about 2%-3%. The sugars in date syrup may include, but are not limited to fructose, glucose, and sucrose. In the present method, the date syrup may include a volume of fructose relative to the total volume of date syrup of about 15%-20%, or about 17%-18%. In the present method, the date syrup may include a volume of glucose relative to the total volume of date syrup of about 20%-40%, about 22%-38%, about 25%-35%, or about 28%-32%. In the present method, the date syrup may include a volume of sucrose relative to the total volume of date syrup of about 0.1%-50%, about 0.5%-45%, about 1%-35%, about 5%-30%, about 10%-25%, or about 15%-20%. The date syrup may further include tannins, citric acid, and pectin at a volume relative to the total volume of date syrup of about 0.1%-10%, about 0.5%-8%, about 1%-5%, or about 2%-4%. In some implementations of the method, the date syrup comprises at least one polyphenol selected from the groups consisting of caffeoylshikimic acid hexoside, caffeoyl-sinapoyl monohexoside, and caffeoyl-sinnapoyl dihexoside. The date syrup may include a volume of polyphenol relative to the total volume of date syrup of about 0.1%-20%, about 0.5%-18%, about 1%-15%, about 2%-12%, about 3%-10%, about 4%-9%, about 5%-8%, or about 6%-7%. In some implementations of the method, the date syrup may further comprise a fatty acid such as palmitic acid, linoleic acid, or linolenic acid. The date syrup may include a volume of fatty acids relative to the total volume of date syrup of about 0.1%-5%, about 0.25%-4.5%, about 0.5%-4%, about 0.75%-3.5%, about 1%-3%, or about 1.5%-2.5%.

In some implementations of the method, the growth medium may further include molasses and/or palm sugar. Either molasses and/or palm sugar may be in a volume/volume ratio relative to a volume of a culture of the bacteria of about 0.1%-5%, about 0.5%-5%, about 1%-4%, or about 2%-3%.

In some implementations of the method, a level of dissolved oxygen may be between about 0.1%-15%, about 0.5%-12%, about 1%-10%, about 5%-8%, or about 6%-7%. The level of oxygen may directly impact the production efficiency of PHA in the bacteria. Oxygen levels greater than 18% reduce the production efficiency of PHA, thus oxygen levels greater than 18% are excluded from the method of the present disclosure. Further, optionally, any of furfural, vanillin, levulinic acid, acetic acid, halogenated alkylacids, halogenated fatty acids, and halogenated sugars may be excluded from the present method. These compounds are preferably excluded so as to avoid an inhibitory effect on the bacterial enzymes that produce PHA.

In bacteria, the PHA may form in inclusion bodies. Inclusion bodies are intracellular vesicles surrounded by a lipid membrane. Inclusion bodies often enclose misfolded proteins, protein aggregates, or viral particles. Energy molecules such as glycogen may be stored in inclusion bodies. In some implementations of the present method, the PHA produced in the bacteria of a *Bacillus* species may accumulate in an intracellular inclusion body of the bacteria. In some implementations of the method, PHB granules may be released into the medium.

The growth media in which the bacteria grows and expresses the PHA may include additional nutrients and minerals. In some implementations of the method, the growth medium may include nutrient broth, magnesium sulfate heptahydrate, and/or a trace element solution. The growth media may further include ammonium sulfate, disodium phosphate dodecahydrate, calcium chloride dihydrate, and/or ferrous sulfate heptahydrate. The nutrient broth may have a concentration of about 0.1 g/L-10 g/L, about 0.5 g/L-9.5 g/L, about 1 g/L-9 g/L, about 1.5 g/L-8.5 g/L, about 2 g/L-8 g/L, about 2.5 g/L-7.5 g/L, about 3 g/L-7 g/L, about 3.5 g/L-6.5 g/L, about 4 g/L-6 g/L, or about 4.5 g/L-5.5 g/L per volume of the growth medium. The ammonium sulfate may have a concentration of about 0.1 g/L-5 g/L, about 0.5 g/L-4.5 g/L, about 1 g/L-4 g/L, about 1.5 g/L-3.5 g/L, about 2 g/L-3 g/L per volume of the growth medium. The disodium phosphate dodecahydrate may have a concentration of about of about 0.1 g/L-5 g/L, about 0.5 g/L-4.5 g/L, about 1 g/L-4 g/L, about 1.5 g/L-3.5 g/L, about 2 g/L-3 g/L per volume of the growth medium. The magnesium sulfate heptahydrate may have a concentration of about of about 0.1 g/L-1 g/L, about 0.2 g/L-0.9 g/L, about 0.3 g/L-0.8 g/L, about 0.4 g/L-0.7 g/L, or about 0.5 g/L-0.6 g/L per volume of the growth medium. The calcium chloride dihydrate may have a concentration of about of about 0.1 g/L-2 g/L, about 0.2 g/L-1.9 g/L, about 0.3 g/L-1.8 g/L, about 0.4 g/L-1.7 g/L, about 0.5 g/L-1.6 g/L, about 0.6 g/L-1.5 g/L, about 0.7 g/L-1.4 g/L, about 0.8 g/L-about 1.3 g/L, about 0.9 g/L-1.2 g/L, about 1 g/L-1.1 g/L per volume of the growth medium. The ferrous sulfate heptahydrate may have a concentration of about 0.001 g/L-2 g/L, about 0.05 g/L-1.9 g/L, about 0.1 g/L-1.8 g/L, about 0.5 g/L-1.7 g/L, about 0.6 g/L-1.6 g/L, about 0.7 g/L-1.5 g/L, about 0.8 g/L-1.4 g/L, about 0.9 g/L-1.3 g/L, or about 1 g/L-1.2 g/L per volume of the growth medium. The trace element solution may have a volume/volume ratio in the growth medium of about 1 mL/L-5 mL/L, about 1.5 mL/L-4.5 mL/L, about 2 mL/L-4 mL/L, or about 2.5 mL/L-3.5 mL/L. The growth medium may be a pH of about 6.9-7.4, about 6.95-7.35, about 7-7.3, about 7.05-7.25, or about 7.1-7.2.

In some implementations of the method, the trace element solution may include, but is not limited to zinc sulfate heptahydrate, manganese chloride tetrahydrate, and copper sulfate tetrahydrate. The trace element solution may further include boric acid, cobalt chloride hexahydrate, and sodium molybdate dihydrate. Trace elements may be important to the bacteria health by providing structural support to nucleic acids or regulation and activity of bacterial enzymes. A concentration of the zinc sulfate heptahydrate in the trace element solution may be about 0.05 g/L-1 g/L, about 0.1 g/L-0.9 g/L, about 0.2 g/L-0.8 g/L, about 0.3 g/L-0.7 g/L, or about 0.4 g/L-0.6 g/L. A concentration of the boric acid in the trace element solution may be about 0.1 g/L-1.5 g/L, about 0.2 g/L-1.4 g/L, about 0.3 g/L-1.3 g/L, about 0.4 g/L-1.2 g/L, about 0.5 g/L-1.1 g/L, about 0.6 g/L-1.0 g/L, or about 0.7 g/L-0.9 g/L. A concentration of the manganese chloride tetrahydrate in the trace element solution may be about 0.01-1.0 g/L, about 0.1 g/L-0.9 g/L, about 0.2 g/L-0.8 g/L, about 0.3 g/L-0.7 g/L, about 0.4 g/L-0.6 g/L. A concentration of the cobalt chloride hexahydrate in the trace element solution may be about 0.1 g/L-1.5 g/L, about 0.2 g/L-1.4 g/L, about 0.3 g/L-1.3 g/L, about 0.4 g/L-1.2 g/L, about 0.5 g/L-1.1 g/L, about 0.6 g/L-1.0 g/L, or about 0.7 g/L-0.9 g/L. A concentration of the copper sulfate tetrahydrate in the trace element solution may be about 0.01-1.0 g/L, about 0.1 g/L-0.9 g/L, about 0.2 g/L-0.8 g/L, about 0.3 g/L-0.7 g/L, about 0.4 g/L-0.6 g/L. A concentration of the sodium molybdate dihydrate in the trace element solution may be about 0.01-1.0 g/L, about 0.1 g/L-0.9 g/L, about 0.2 g/L-0.8 g/L, about 0.3 g/L-0.7 g/L, about 0.4 g/L-0.6 g/L.

In some implementations of the method the growth media may further include non-sugar ingredients, which may enhance and support PHAs production by *Bacillus* sp. The non-sugar ingredients may include, but are not limited to vitamin B complex, calcium, phosphate, iron, and magnesium. Each non-sugar ingredient may be included in the growth media in a concentration of about 0.001-1.0 g/L, about 0.01 g/L-0.9 g/L, about 0.1 g/L-0.8 g/L, about 0.3 g/L-0.7 g/L, about 0.4 g/L-0.6 g/L. The enhancement of PHAs produced as a result of adding at least one non-sugar ingredient relative to PHAs produced without adding the non-sugar ingredient to the growth media may be an increase of 1%-20%, 2%-18%, 5%-15%, or 8%-12%.

In some implementations of the method, the culturing includes growing the bacteria at a growth temperature of about 25° C.-38° C., about 26° C.-36° C., or about 27° C.-32° C., and under agitation in a fed-batch process vessel. The agitation may be accomplished by methods including, but not limited to mixing by baffle attached to an impeller, pulsed-jet mixer, or close-clearance mixers. For bacterial cultures, mixing increases circulation and reduces settling in the fed-batch process vessel.

In some implementations of the method, the culturing further includes growing the bacteria in a fed-batch phase for about 20 hours-84 hours, about 22 hours-72 hours, about 24 hours-68 hours, about 26 hours-66 hours, about 28 hours-64 hours, about 30 hours-62 hours, about 32 hours-60 hours, about 34 hours-58 hours, about 36 hours-56 hours, about 38 hours-54 hours, about 40 hours-52 hours, about 42 hours-50 hours, or about 44 hours-48 hours. During the fed-batch phase the date syrup is administered to the bacteria at a limiting level to force the bacteria to synthesize PHA. The date syrup may be a final concentration in the growth media of about 5 g/L-50 g/L, 8 g/L-40 g/L, 10 g/L-30 g/L, or 15 g/L-20 g/L In some implementations of the method, the limiting level of the date syrup relative to a volume of the bacteria in the fed-batch process vessel may be a volume/volume ratio of about 0.1%-5%, about 0.5%-4.5%, about 0.75%-4%, about 1%-3.5%, about 1.25%-3.25%, about 1.5%-3%, about 1.75%-2.75%, or about 2%-2.5%.

In some implementations of the method, the limiting level of the date syrup may be administered in a pulse feeding, a shot feeding, a linearly modulated feeding, an exponentially modulated feeding, or a constant feeding during the fed-batch phase. The pulse feeding may be described as administering date syrup to the bacteria in an interrupted sequence in which a concentration administered at each pulse is constant. The shot feeding may be described as administering date syrup in one dose to the bacteria. The linearly modulated feeding may be described as uninterruptedly introducing date syrup to the bacteria in a concentration that linearly increases or linearly decreases over a period of time. The exponentially modulated feeding may be described as uninterruptedly introducing date syrup to the bacteria in a concentration that exponentially increases or exponentially decreases over a period of time. The constant feeding may be described as maintaining a continuous administration of an unchanging concentration of the date syrup over a period of time.

After the fed-batch phase duration, the PHA may be preserved from degradation by reducing the growth temperature in the fed-batch process vessel containing the cultured bacteria. In some implementations, the growth temperature is reduced to an ambient temperature after the fed-batch phase of about 20° C.-25° C., about 21° C.-24° C., or about 22° C.-23° C.

Once the growth temperature is reduced the PHA must be isolated from the inclusion bodies inside each bacteria. In some implementations of the method, the isolating includes separating the bacteria from the growth media, which may be accomplished by settling of the bacteria, by centrifuge, or a combination of both. Following separating the bacteria from the growth media, the bacteria is resuspended in a detergent media. The detergent media may include, but is not limited to at least one detergent selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethyl-ammonio)-1-propanesulfonate, and n-Octyl-β-D-thioglucopyranoside, a chaotropic agent, and a buffer. The chaotropic agent is a substance which disrupts the structure of, and denatures, macromolecules such as proteins and nucleic acids (e.g. DNA and RNA). Chaotropic solutes increase the entropy of the system by interfering with intramolecular interactions mediated by non-covalent forces such as hydrogen bonds, van der Waals forces, and hydrophobic effects. An increase in chaotropic solutes in a biological system will denature macromolecules, reduce enzymatic activity and induce stress on a cell. The chaotropic agent may include, but is not limited to butanol, ethanol, guanidinium chloride, lithium perchlorate lithium acetate, magnesium chloride, phenol, propanol, sodium dodecyl sulfate, thiourea, or urea. The buffer may be a pH of about 5-8, about 5.5-7.5, about 6-7. In some implementations of the method, the detergent media further includes a lysozyme, which is an enzyme that catalyzes reactions that break down a bacterial cell wall. The detergent media may disrupt and weaken the cell walls and membranes of the bacteria, to break open a bacteria and expose the inclusion bodies containing PHA.

After adding the detergent media, freezing the bacteria in the detergent media may allow water molecules to crystallize and weaken the inclusion body membrane. In some implementations of the method, a temperature of the freezing is about −50° C.–−80° C., about −55° C.–−78° C., about −60° C.–−76° C., about −65° C.–−74° C., or about −70° C.–−72° C. Following freezing, rapidly reheating may lyse the bacteria in the detergent media. The detergent media containing the bacteria may be reheated to about 30° C.–40° C., about 32° C.–38° C., about 34° C.–36° C. Reheating the bacteria may break membranes and denature membrane proteins.

After reheating, sonicating the lysed bacteria in the detergent media may further disperse a membrane surrounding the inclusion body, which releases the PHA into the solution. The sonicating may be at a frequency of about 15 kHz-50 kHz, about 20 kHz-40 kHz, about 25 kHz-35 kHz, or about 28 kHz-32 kHz.

Once the bacteria are lysed, a supernatant comprising the PHA may be separated by filtering, centrifugation, or settling. Some implementations of the method include adding a secondary detergent to the lysed bacteria in the detergent media to additionally break down membranes and dissociate agglomerated proteins around the inclusion body, before separating the supernatant from the lysed bacteria. In some implementations of the method, the secondary detergent is selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethylammonio)-1-propanesulfonate, and n-Octyl-β-D-thioglucopyranoside. A second sonicating may follow the addition of the secondary detergent, as described herein.

Upon collecting the supernatant the PHA may be analyzed by mass spectrometry, NMR, HPLC, or other methods known to those familiar in the art. PHA may be concentrated from the supernatant and put to use as a biodegradable polymer.

---

---

The invention claimed is:

1. A method for producing a polyhydroxyalkanoate comprising:
    fed-batch culturing *Bacillus* bacteria suspended in a culture medium containing date syrup,
    separating the cultured bacteria from the growth medium,
    lysing the separated cultured bacteria, and
    isolating the polyhydroxyalkanoate;
    wherein said *Bacillus* bacteria comprise a polynucleotide at least 95% identical to that described by GENBANK accession number HQ124332 (SEQ ID NO: 1).

2. The method of claim 1, wherein the growth medium consists essentially of about 0.5 to 7% date syrup by volume based on a total volume of the growth medium, trace minerals and other non-sugar ingredients.

3. The method of claim 1, wherein the date syrup comprises 1-90% v/v sugars, 1-10% v/v protein and 0.1-5% ash based on the total volume of the date syrup.

4. The method of claim 1, wherein the date syrup comprises 15-20% by volume of fructose, 20-40% by volume of glucose, and 0.1 to 50% by volume of sucrose.

5. The method of claim 1, wherein the growth medium contains no more than 10% v/v of tannins, citric acid or pectin; and wherein furfural, vanillin, levulinic acid, acetic acid, halogenated alkylacids, halogenated fatty acids, and halogenated sugars are not incorporated into it.

6. The method of claim 1, wherein the growth medium further comprises 0.1%-5% v/v molasses or palm sugar, relative to the total volume of the growth medium.

7. The method of claim 1, wherein the growth medium has a pH ranging from 6.9 to 7.4 and comprises 0.1 g/L-10 g/L of a nutrient broth other than date syrup containing 0.1 g/L-1 g/L of magnesium sulfate heptahydrate.

8. The method of claim 1, wherein the growth medium has a pH ranging from 6.9 to 7.4 and comprises 0.1 g/L-10 g/L of a nutrient broth other than date syrup containing 0.1 g/L-1 g/L of magnesium sulfate heptahydrate, 0.05 g/L-1 g/L of zinc sulfate heptahydrate, 0.01-1.0 g/L of manganese chloride tetrahydrate, and 0.01 g/L-1.0 g/L copper sulfate tetrahydrate.

9. The method of claim 1, wherein the culturing comprises growing the bacteria at a growth temperature of 25° C.-38° C. under mechanical agitation in a fed-batch process vessel.

10. The method of claim 1, wherein the bacteria are forced to synthesize polyhydroxyalkanoate by culturing in a fed-batch process vessel for a period of 20 to 84 hours in a fed-batch phase in which the date syrup is added to the growth medium at a limiting level of 0.1%-5% v/v relative to a volume of the bacteria or at a limiting level of 5 to 50 g/L based on the volume of the growth medium.

11. The method of claim 1, wherein the bacteria are forced to synthesize polyhydroxyalkanoate by culturing in a fed-batch process vessel for a period of 20 to 84 hours in a fed-batch phase in which the date syrup is added to the growth medium at a limiting level of 0.1%-5% v/v relative to a volume of the bacteria or at a limiting level of 5 to 50 g/L based on the volume of the growth medium; wherein the limiting level is administered by a pulse, a shot feeding, a linearly modulated feeding, an exponentially modulated feeding, or a constant feeding during fed-batch culturing.

12. The method of claim 1, wherein the culturing further comprises reducing the growth temperature to an ambient temperature of 20° C.-24° C. after a fed-batch phase.

13. The method of claim 1, wherein isolating the polyhydroxyalkanoate comprises recovering intracellular inclusion bodies and dispersing membranes surrounding the inclusion bodies to recover the polyhydroxyalkanoate.

14. The method of claim 1, wherein isolating the polyhydroxyalkanoate comprises:
separating the bacteria from the growth media;
resuspending the bacteria in a detergent media, optionally containing lysozyme;
freezing the bacteria in the detergent media;
warming the bacteria in the detergent media to 30° C.-40° C. to lyse the bacteria;
sonicating the lysed bacteria in the detergent media optionally in the presence of a secondary detergent; and
separating the supernatant from the lysed bacteria.

15. The method of claim 14, wherein the separating comprises centrifugation, settling, and/or filtration.

16. The method of claim 14, wherein the detergent medium for sonicating the lysed bacteria further comprises at least one secondary detergent selected from the group consisting of polyethylene glycol sorbitan monolaurate, 4-(1,1,3,3-tetramethylbutyl)phenyl-polyethylene glycol, sodium dodecyl sulfate, 3-((3-cholamidopropyl) dimethylammonio)-1-propanesulfonate, and n-Octyl-β-D-thioglucopyranoside.

17. The method of claim 14, wherein the detergent media further comprises at least One chaotropic agent selected from the group consisting of butanol, ethanol, guanidinium chloride, lithium perchlorate, lithium acetate, magnesium chloride, phenol, propanol, thiourea, and urea and a buffer that provides a pH of 5 to 8.

18. The method of claim 14, further comprising sonicating after adding the secondary detergent.

19. The method of claim 14, wherein the polyhydroxyalkanoate is a polyhydroxybutyrate.

20. The method of claim 14, wherein the polyhydroxyalkanoate is a polyhydroxyvalerate.

* * * * *

SEQUENCE LISTING

<160> NUMBER OF SEQ ID NOS: 1

<210> SEQ ID NO 1
<211> LENGTH: 684
<212> TYPE: DNA
<213> ORGANISM: Bacillus megaterium

<400> SEQUENCE: 1

```
taacgcatta agcactccgc ctggggagta cggtcgcaag actgaaactc aaaggaattg      60 acggggccc gcacaagcgg tggagcatgt ggtttaattc gaagcaacgc gaagaacctt     120
accaggtctt gacatcctct gacaactcta gagatagagc gttcccttc gggggacaga     180 gtgacaggtg gtgcatggtt gtcgtcagct cgtgtcgtga gatgttgggt taagtcccgc     240
aacgagcgca acccttgatc ttagttgcca gcatttagtt gggcactcta aggtgactgc     300
cggtgacaaa ccggaggaag gtggggatga cgtcaaatca tcatgcccct tatgacctgg     360
gctacacacg tgctacaatg gatggtacaa agggctgcaa gaccgcgagg tcaagccaat     420
cccataaaac cattctcagt tcggattgta ggctgcaact cgcctacatg aagctggaat     480
cgctagtaat cgcggatcag catgccgcgg tgaatacgtt cccgggcctt gtacacaccg     540
cccgtcacac cacgagagtt tgtaacaccc gaagtcggtg gagtaaccgt aaggagctag     600
ccgcctaagg tgggacagat gattggggtg aagtcgtaac aaggtagccg tatcggaagg     660
tgcggctgga tcacctcctt tcta                                            684
```